US00PP31771P2

(12) United States Plant Patent
Cain

(10) Patent No.: US PP31,771 P2
(45) Date of Patent: May 19, 2020

(54) GRAPEVINE PLANT NAMED 'IFG FORTY-ONE'

(50) Latin Name: ***Vitis interspecific* hybrid**
Varietal Denomination: IFG Forty-one

(71) Applicant: David Cain, Bakersfield, CA (US)

(72) Inventor: David Cain, Bakersfield, CA (US)

(73) Assignee: INTERNATIONAL FRUIT GENETICS, LLC, Bakersfield, CA (US)

( * ) Notice: Subject to any disclaimer, the term of this patent is extended or adjusted under 35 U.S.C. 154(b) by 0 days.

(21) Appl. No.: 16/501,404

(22) Filed: Apr. 9, 2019

(51) Int. Cl.
*A01H 5/08* (2018.01)
*A01H 6/88* (2018.01)

(52) U.S. Cl.
USPC ..... Plt./205
CPC ..... *A01H 6/88* (2018.05)

(58) Field of Classification Search
USPC ..... Plt./205
CPC ..... A01H 6/88; A01H 5/08
See application file for complete search history.

(56) References Cited

U.S. PATENT DOCUMENTS

PP28,667 P3 11/2017 Cain

*Primary Examiner* — Keith O. Robinson

(57) ABSTRACT

This invention is a new and distinct grapevine variety denominated 'IFG Forty-one'. The new grapevine is characterized by producing small naturally seedless red berries having a broad ellipsoid shape with a unique combination of muscat and labrusca flavor. The strong fruity flavor is reminiscent of strawberries. Fruits normally ripen mid-season.

1 Drawing Sheet

Latin name of the genus and species claimed: *Vitis interspecific* hybrid.

Variety denomination: 'IFG FORTY-ONE'.

BACKGROUND OF THE INVENTION

The new and distinct grapevine plant described and claimed herein originated from a hand pollinated cross of '04098-027-083' (*Vitis vinifera* selection from the IFG breeding program) and interspecific hybrid IFG Twenty-three (U.S. Plant Pat. No. 28,667), hybridized in May 2011. The abortive seed traces were subsequently embryo cultured and the resulting 109 seedlings were planted in the field in April 2012. The present variety of grapevine was selected as a single plant in September 2014 and was first asexually propagated by hardwood cuttings in December 2014 near Delano, Kern County, Calif. These resulting cuttings produced second generation plants that were planted during April 2015 near Delano, Kern County, Calif. and were observed for three years and found to reproduce true-to-type.

BRIEF SUMMARY OF THE INVENTION

The new grapevine plant 'IFG Forty-one' is characterized by producing small naturally seedless red berries having a broad ellipsoid shape with a unique combination of muscat and labrusca flavor. The strong fruity flavor is reminiscent of strawberries. Fruits normally ripen mid-season, about mid to late August near Delano Calif. Fruits are fairly low in acidity, with medium dense, firm texture. Berries color readily even in hot climatic conditions and produce completely colored dark red berries. Vines are very productive and can be pruned to short spurs. Clusters are medium size, moderately loose, and require sizing with gibberellic acid to enlarge berry size.

The new grapevine differs from its maternal parent, the '04098-027-083' selection by having dark red rather than light red berries and by having a broad ellipsoid rather than a narrower elliptic berry shape of '04098-027-083'. 'IFG Forty-one' has a labrusca flavor rather than a muscat flavor of '04098-027-083'. 'IFG Forty-one' can be distinguished from its pollen parent, 'IFG Twenty-three', by having a smaller berry size with a broad ellipsoid shape as opposed to the larger berry with a round shape of the 'IFG Twenty-three'. 'IFG Forty-one' has smaller, less noticeable seed traces than the 'IFG Twenty-three'. 'IFG Forty-one' also has a weaker less rampant vine growth habit than the 'IFG Twenty-three' and has sparse density of erect hairs on the main veins of the lower leaf surface compared to the dense erect hairs on the main veins of the lower leaf surface on 'IFG Twenty-three'.

'IFG Forty-one' is most similar to 'IFG Twenty-one' (U.S. Plant Pat. No. 26,541). 'IFG Forty-one' differs from 'IFG Twenty-one' by having darker red berry color, larger berry size and by ripening approximately three weeks later.

BRIEF DESCRIPTION OF THE DRAWING

The accompanying photographic drawing illustrates in full color 'IFG Forty-one', taken from a 3-year-old vine. The photograph was taken outdoors with indirect lighting. The colors are as nearly true as is reasonably possible in a color representation of this type.

The left side of the drawing has a mature leaf.

A mature fruit cluster is represented in the center of the drawing along with a typical berry in cross section.

A young shoot tip can be seen on the right side of the drawing.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published in 2016 by The Royal Horticultural Society, London, England.

Throughout this specification, subjective description values conform to those set forth by the UPOV International Union for the Protection of New Varieties of Plants publication 'Grapevine *Vitis* L. Guidelines'.

The descriptive matter which follows pertains to 3-year-old plants of 'IFG Forty-one' grown in the vicinity of Delano, Kern County, Calif. during 2018, and is believed to apply to plants of the variety grown under similar conditions of soil and climate elsewhere:

VINE

General:

*Vigor*.—Moderately vigorous.
*Density of foliage*.—Medium.
*Productivity*.—Moderately productive, producing about 12.5 to 18.8 kg of fruit per vine.
*Root stock*.—Own root.
*Training method*.—Typically spur pruned leaving 2 bud spurs.

Trunk:

*Trunk diameter of* 3-*year-old vines at* 30 *cm above the soil line*.—Approximately 4.1 cm.
*Shape*.—Medium to slender.
*Straps*.—Very long, continuous.
*Surface texture*.—Medium rough texture.
*Inner bark color*.—Greyed-orange: 165A.
*Outer bark color*.—The following colors were observed: Brown: N200A and N200B.

SHOOTS

Young shoot:

*Form of tip*.—Fully opened.
*Distribution of anthocyanin coloration of tip*.—Absent.
*Intensity of anthocyanin coloration of tip*.—Absent.
*Density of prostrate hairs of tip*.—Sparse.
*Density of erect hairs on tip*.—Absent.
*Color*.—Yellow-green: N144A.

Woody shoot (mature canes):

*Internode length*.—Medium: About 8.9 cm.
*Width at node*.—About 12.3 mm.
*Cross section*.—Circular.
*Surface*.—Striate.
*Main color*.—The following colors were observed: Greyed-orange: 165A and 165B.
*Density of erect hairs on nodes*.—None or very sparse.
*Density of erect hairs on internodes*.—None or very sparse.
*Axillary shoot vigor at full bloom*.—Weak.

Flowering shoot:

*Color*.—dorsal side of internodes — Yellow-green: 144A.
*Color*.—ventral side of internodes — Yellow-green: 144A.
*Color*.—dorsal side of nodes — Yellow-green: 144A.
*Color*.—ventral side of nodes — Yellow-green: 144A.
*Density of prostrate hairs on nodes*.—Medium to sparse.
*Density of erect hairs on nodes*.—None.
*Density of prostrate hairs on internode*.—Sparse.
*Density of erect hairs on internode*.—None to very sparse.
*Anthocyanin coloration of buds*.—Absent.

Tendrils:

*Distribution on the shoot* (*at full flowering*).—Discontinuous.
*Color*.—Yellow-green: N144A.
*Form*.—Bifurcated and trifurcated.
*Number of consecutive tendrils*.—2.

LEAVES

Young leaves:

*Color of upper surface of first four distal unfolded leaves*.—Yellow-green: N144A.
*Color of lower surface of young leaves*.—Yellow-green: 146A.
*Average intensity of anthocyanin coloration of six distal leaves prior to flowering*.—Absent.
*Density of prostrate hairs between veins* (*lower surface*).—Very sparse.
*Density of prostrate hairs on veins* (*lower surface*).—Sparse.
*Density of erect hairs between veins* (*lower surface*).—Absent.
*Density of erect hairs on veins* (*lower surface*).—Very sparse.

Mature leaves (opposite first cluster):

*Average length*.—About 12.0 cm.
*Average width*.—About 16.2 cm.
*Mature leaf size*.—Medium large.
*Shape of blade*.—Pentagonal.
*Number of lobes*.—5.
*Blade venation*.—Palmate.
*Anthocyanin coloration of main veins on upper side of blade*.—Absent.
*Mature leaf profile*.—Undulate.
*Blistering surface of blade upper surface*.—Weak to medium.
*Leaf blade tip*.—In the plane of the leaf.
*Leaf apex*.—Acute.
*Leaf margin*.—Serrate.
*Undulation of margin*.—Slight.
*Undulation of blade between main and lateral veins*.—Slight undulation over entire area.
*Shape of teeth*.—Mixture of both sides straight and both sides convex.
*Length of teeth of secondary veins*.—About 0.6 cm.
*Ratio length to width of teeth of secondary veins*.—About 1:2.
*Shape of upper lateral sinuses*.—Lobes slightly to strongly overlapping.
*Depth of upper lateral sinuses*.—Medium.
*General shape petiole sinus*.—Half open.
*Shape of base of upper leaf sinuses*.—U-shaped.
*Tooth at petiole sinus*.—Absent.
*Density of prostrate hairs between veins on lower surface of blade*.—Very sparse.
*Density of erect hairs between veins on lower surface of blade*.—Absent.

*Density of prostrate hairs on main veins on lower surface of blade*.—Sparse.
*Density of erect hairs on main veins on lower surface of blade*.—Sparse.
*Density of prostrate hairs on main veins on upper surface of blade*.—Sparse.
*Density of erect hairs on main veins on upper surface of blade*.—Sparse.
*Autumn coloration of leaves*.—Leaves can be a single color or combination of colors, in a mottled pattern or on the edges of the leaves. The following colors were observed: Greyed-yellow: 162A and 162B and Greyed-purple: 184A and 184B and 184C and 187A and 187B and Greyed-red: 179B and 179C.

Upper surface:
*Color*.—Green: 137A.
*Anthocyanin coloration of main veins* (*lower surface*).—Absent.
*Color of main veins*.—Yellow-green: 144B.
*Surface appearance*.—Semi-glossy.
*Blistering surface of blade*.—Medium.

Lower surface:
*Color*.—The following colors were observed: Yellow-green: 146A.
*Anthocyanin coloration of main veins* (*lower surface*).—Absent.
*Color of main veins*.—Yellow-green: 145C.
*Glossiness*.—Weak.
*Surface texture*.—Rugose.
*Surface appearance*.—Dull.

Petiole:
*Length*.—About 10.5 cm.
*Diameter of petiole* 2 *cm from blade*.—About 3.2 mm.
*Petiole color*.—The following colors were observed: Yellow-green: 145B and Red-purple: 59D.
*Length of petiole compared to middle vein*.—Slightly shorter.
*Density of prostrate hairs on petiole*.—None or very sparse.
*Density of erect hairs on petiole*.—None.

Buds:
*Bud fruitfulness*.—Basal: mostly fruitful.
*Position of first fruitful shoot on previous season cane*.—$1^{st}$ to $2^{nd}$ node.
*Dormant bud length*.—About 5.0 mm.
*Dormant bud width in the proximal/distal plane*.—About 3.4 mm.
*Dormant bud color*.—The following colors were observed: Greyed-orange: 166A and 166B.
*Time of bud burst*.—Midseason: About Mar. 19, 2018.

FLOWERS

General:
*Flower sex*.—Hermaphrodite.
*Length of single flower, unopened*.—About 3.0 mm.
*Width of single flower*.—Unopened: About 1.9 mm. Opened: About 5.6 mm.
*Stamen length*.—About 2.8 mm.
*Stamen count*.—5.
*Pollen color*.—Yellow: 10A.
*Pistil length*.—About 2.4 mm.
*Pistil color*.—Yellow-green: 144A.
*Position of first flowering and fruiting node*.—$3^{rd}$ to $4^{th}$ node (current season growth).
*Number of inflorescence per flowering shoot*.—1.1 to 2: About 1.3.
*Time of bloom*.—Early to mid-season as compared with similar varieties in the growing area of Delano, Calif.
*Date of full bloom*.—About May 7, 2018.

FRUIT

General:
*Ripening period*.—Mid-season: Approximately Aug. 22, 2018.
*Use*.—Fresh market.
*Keeping quality*.—Good, remains commercially acceptable when stored up to 8 weeks at 0° C. and high Relative humidity.
*Refractometer test*.—Soluble solids: About 19.2 Brix.
*Brix/acid*.—About 58.2%.
*Titratable acidity*.—About 0.33.
*Juice ph*.—About 3.55.
*Juice color*.—Greyed-orange: 174C.

Cluster:
*Mature cluster length* (*peduncle excluded*).—About 23.7 cm.
*Mature cluster width*.—About 13.5 cm.
*Mature cluster weight*.—About 418 g.
*Bunch density*.—Loose: single berries, some pedicels visible.
*Number of berries*.—About 130.
*Form*.—Conical.

Peduncle:
*Lignification of peduncle*.—Weak.
*Diameter of peduncle*.—About 0.5 cm.
*Length of peduncle*.—Medium: Approximately 5.7 cm.
*Color of peduncle*.—Yellow-green: 144B.

Berry:
*Uniformity of size*.—Uniform.
*Single berry weight*.—About 3.7 g natural; to about 5.3 g when treated with gibberellic acid.
*Shape*.—Broad ellipsoid.
*Seeds*.—Contains small rudimentary seed traces.
*Cross section*.—Circular.
*Berry dimensions*.—Longitudinal axis: About 2.0 cm; horizontal axis: About 1.7 cm.
*Pedicel length*.—About 6.6 mm.
*Pedicel width*.—About 1.3 mm.
*Pedicel color*.—Yellow-green: 144B.
*Berry firmness*.—Firm.
*Particular flavor*.—Combination of muscat and labrusca reminiscent of strawberries.
*Bloom* (*cuticular wax*).—Medium.
*Berry separation from pedicel*.—Moderate.
*Skin color* (*without bloom*).—The following colors were observed: Greyed-purple: 187B and 187C.
*Flesh color*.—Greyed-green: 19B.

Skin:
*Thickness*.—Medium.
*Skin toughness*.—Not notable when chewing.
*Reticulation*.—Absent.
*Tenacity*.—Tenacious to flesh.

What is claimed:

1. A new and distinct variety of grapevine plant as herein illustrated and described.

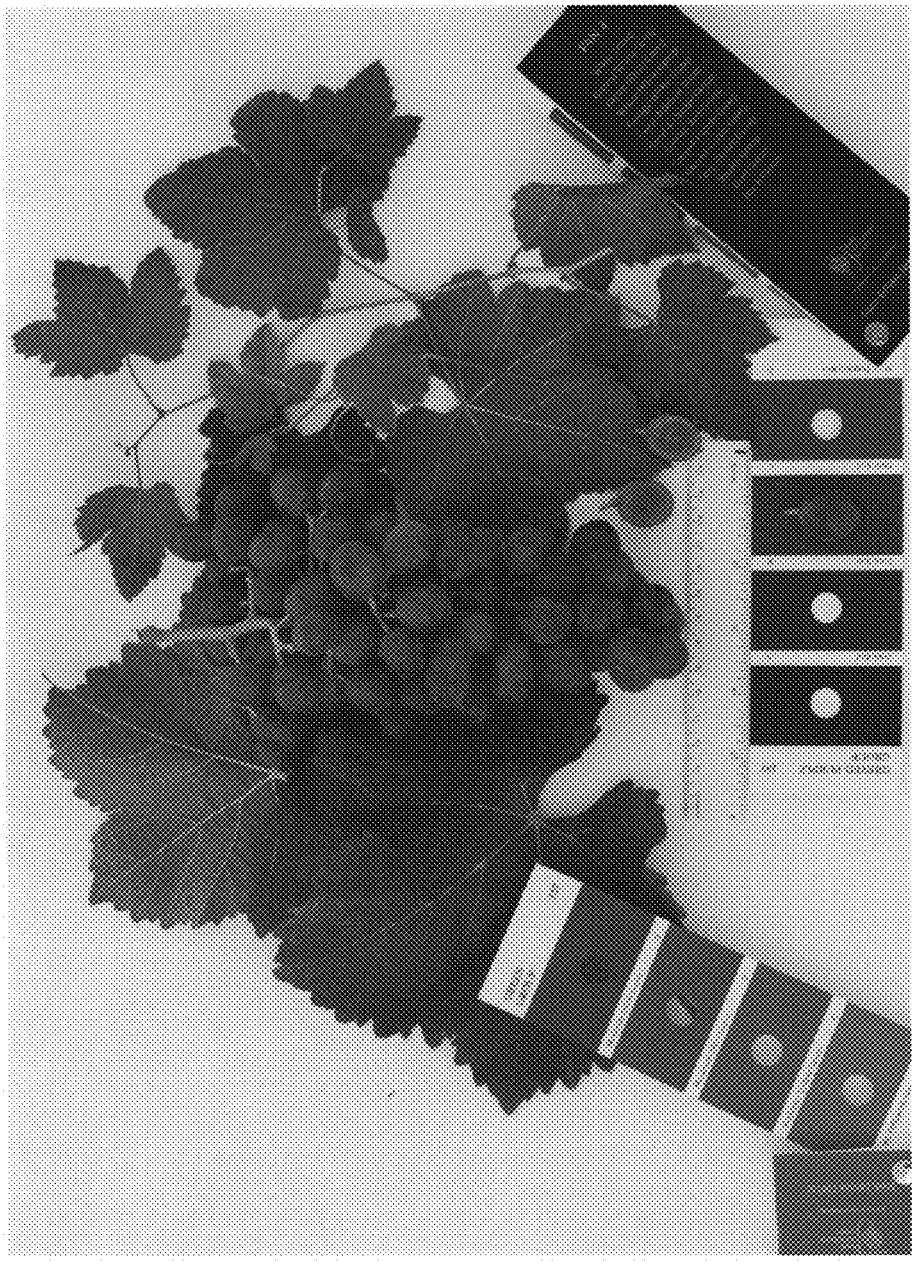

* * * * *